(12) United States Patent
Cavazza

(10) Patent No.: US 6,328,998 B1
(45) Date of Patent: *Dec. 11, 2001

(54) COMPOSITION COMPRISING L-CARNITINE OR AN ALKANOYL L-CARNITINE AND LONG-CHAIN ALKANOLS

(75) Inventor: Claudio Cavazza, Rome (IT)

(73) Assignee: Sigma-Tau Industrie Farmaceutiche Riunite S.p.A., Rome (IT)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/462,169

(22) PCT Filed: Jul. 9, 1998

(86) PCT No.: PCT/IT98/00190

§ 371 Date: Jan. 3, 2000

§ 102(e) Date: Jan. 3, 2000

(87) PCT Pub. No.: WO99/06039

PCT Pub. Date: Feb. 11, 1999

(30) Foreign Application Priority Data

Aug. 1, 1997 (IT) .............................. RM97A0487

(51) Int. Cl.$^7$ .................. A01N 65/00; A01N 37/30; A01N 31/00; A61K 35/78
(52) U.S. Cl. .................. 424/725; 424/750; 514/547; 514/556; 514/724; 514/729; 514/734
(58) Field of Search ................. 424/195.1, 316, 424/319, 750, 752, 725; 514/556, 474, 458, 164, 547, 724, 729, 734

(56) References Cited

U.S. PATENT DOCUMENTS

| | | | |
|---|---|---|---|
| 4,751,242 | * | 6/1988 | Calvani et al. . |
| 5,447,959 | * | 9/1995 | Borg . |
| 5,503,831 | * | 4/1996 | Takahashi . |
| 5,560,928 | * | 10/1996 | DeFelice . |
| 5,856,316 | * | 1/1999 | Laguna Granja et al. . |
| 5,998,474 | * | 12/1999 | Cavazza . |

FOREIGN PATENT DOCUMENTS

| | | | |
|---|---|---|---|
| 0797993 A | * | 3/1996 | (IT) . |
| 0773020A2 | * | 5/1997 | (IT) . |
| 62099323A | * | 5/1987 | (JP) . |
| 05310563 | * | 11/1993 | (JP) . |
| 05310563 | * | 5/1997 | (JP) . |
| 0439544B1 | * | 10/1989 | (WO) . |
| 0773020A2 | * | 5/1997 | (WO) . |

OTHER PUBLICATIONS

Database WPI Week 9321 Derwent Publications Ltd., London, GB; AN 93–17793 XP002084524 & JP 05 103629 A (Yanamoto), Apr. 27, 1993 see abstract.

Database WPI Week 9321 Derwent Publications Ltd., London, GB; AN 93171762 XP002084525 & JP 05 103596 A (Yanagimoto), Apr. 27, 1993 see abstract.

* cited by examiner

Primary Examiner—Christopher R. Tate
Assistant Examiner—Michele C. Flood
(74) Attorney, Agent, or Firm—Nixon & Vanderhye

(57) ABSTRACT

The use of L-carnitine, some alkanoyl L-carnitines and the pharmacologically acceptable salts thereof in combination with long-chain alkanols such as polycosanols, or polycosanol-bearing natural products or extracts thereof for the prevention and treatment of diseases caused by abnormal lipid metabolism, such as atherosclerosis, hypercholesterolemia, cardiovascular disorders and peripheral diabetic neuropathy.

6 Claims, No Drawings

COMPOSITION COMPRISING L-CARNITINE OR AN ALKANOYL L-CARNITINE AND LONG-CHAIN ALKANOLS

The present invention relates to a pharmaceutical composition for the prevention and treatment of diseases caused by abnormal lipid metabolism or by an increase in platelet aggregation.

Within the context of the populations of the industrialised countries, a slow yet progressive increase in life expectancy is noted; this is not the case only in Italy, but also in other industrialised Western countries and in Japan. The main cause of death in Western countries is to be attributed primarily to diseases of the cardiovascular system, which, in addition to causing death, are also responsible for lengthy periods of hospitalisation and disablement, placing a substantial burden of cost on the national health system.

In Italy, cardiovascular diseases related to abnormal lipid metabolism account for more than 40% of the overall mortality. Our knowledge regarding the relationships between cholesterol and coronary heart disease stems from epidemiological studies conducted in recent years. The conclusions of these studies indicate that the development of severe coronary atherosclerosis and coronary heart disease correlates closely with serum cholesterol levels. Peripheral neuropathies afflict a substantial number of people and, generally speaking, though not causing their deaths, are capable of worsening their quality of life. These pathologies constitute a heterogeneous group of diseases, inasmuch as their aetiology mar be secondary to viral (herpes zoster), ischaemic (atherosclerosis), metabolic (diabetes, kidney and liver failure), toxic (Adriamycin, isoniazide, nitrofurantoin), mechanical (compression, trapping, rupture), radiation and genetic factors as well as to factors related to diseases of the immune system. Moreover, whatever the actual aetiological cause of the disease form, abnormal membrane fluidity is always detectable as a result of an abnormality of cell lipids, cholesterol, gangliosides or platelet aggregation.

Data recently reported in the literature indicate, in fact, that the onset of diabetic peripheral neuropathy is facilitated by increased platelet aggregation.

In cases of hyperlipidaemia, correction of eating habits through an appropriate diet is always the first therapeutic measure. Satisfactory results are not always achieved, however, owing to widespread intolerance of strict alimentary discipline, to the severity of the hypercholesterolaemia, or to genetic-type resistance.

To achieve the desired results in these cases, i.e. normalisation of blood levels of triglycerides and cholesterol, pharmacological treatment has to be resorted to. There are many useful drugs on the market for the treatment of hypertriglyceridaemia and hypercholesterolaemia. The fibrates and statins are the best agents for this purpose, but are not devoid of side effects. The results of experiments in animals and man have suggested that, to reduce cholesterol levels, pharmacological treatment with these two classes of drugs should be given only to patients at high risk for coronary disease in the short term (*JAMA* 1996; 275: 55–60). The polycosanols, which are a mixture of $C_{24}$–$C_{32}$ long-chain aliphatic alcohols ranging from lignoceric acid (tetracosanol) to triacontanol. derived from the wax cuticle of sugar cane, from rice- or wheat-germ oil, or from the leaves of *Ginkgo biloba* or *Ephedra geradina*, are known to be used for the treatment of lipid metabolism disorders both experimentally induced and encountered in clinical practice. A similar favourable effect of polycosanols on platelet aggregation has been found both experimentally and clinically.

The serum triglyceride and serum cholesterol lowering effects of L-carnitine and of a number of alkanoyl L-carnitines are well known; U.S. Pat. No. 4,255,449 and U.S. Pat. No. 4,268,524 describe the use of L-carnitine and alkanoyl L-carnitines. respectively, for normalising abnormally high ratios of low-density lipoproteins (LDL) + very low-density lipoproteins (VLDL) to high-density lipoproteins (HDL), which constitute an aetiological factor in various cardiovascular diseases. Through beta-oxidation of fatty acids, L-carnitine is capable of preventing their accumulation and of supplying the cell energy requirement (Bremner Y, *TIBS* 2, 207, 1977) via modulation of extra- and intra-mitochondrial CoA.

Equally well known is the use of acetyl L-carnitine in the therapeutic treatment of peripheral neuropathies; see, for example, U.S. Pat. No. 4,751,242. L-carnitine and particularly acetyl L-carnitine or propionyl L-carnitine can act by varying the lipid substrate from which the various vasoconstricting and aggregation-promoting factors derive as a result of the effects of cyclo-oxygenase and lipo-oxygenase, by reducing their formation and by promoting the synthesis of antiaggregant and vasodilating factors.

It has now been found unexpectedly that the co-ordinated use —a term which will be precisely defined here below—of L-carnitine or of an alkanoyl L-carnitine in which the linear or branched-chain alkanoyl has 2–6 carbon atoms, or of one of their pharmacologically acceptable salts, in combination with long-chain ($C_{24}$–$C_{30}$) aliphatic alcohols, particularly polycosanols or natural extracts containing polycosanols allows a potent synergistic effect to be achieved in terms of their cholesterolaemia- and triglyceridaemia-lowering and platelet-aggregation inhibiting action.

The well-known lack of toxic and side effects of L-carnitine or of the alkanoyl L-carnitines and polycosanols makes their co-ordinated use according to the invention particularly useful and safe both for the treatment of hypercholesterolaemic and/or hypertriglyceridaemic patients at high risk for cardiovascular disease in the short-, medium- or long term and for the prevention and treatment of diseases related to increased platelet aggregation and to a reduced oxygen concentration (ischaemia), such as, for example, peripheral neuropathies, and diabetic peripheral neuropathy in particular.

In the context of the invention described herein, what is meant by "co-ordinated use" of the afore-mentioned compounds is either their co-administration, i.e. the substantially simultaneous administration of L-carnitine or one of the alkanoyl L-carnitines, or one of their pharmacologically acceptable salts, and of at least one polycosanol, or, indifferently, the administration of a composition containing a combination or mixture of the aforesaid active ingredients, in addition to any excipients included.

The scope of the present invention therefore encompasses both the co-administration of L-carnitine or of an alkanoyl L-carnitine, or one of their pharmacologically acceptable salts, together with polycosanols, and pharmaceutical compositions, which can be administered orally or parenterally, containing a mixture of the two active ingredients.

The polycosanol should preferably be selected from the group comprising triacontanol, hexacontanol, ecocosanol, hexacosanol, tetracosanol, dotriacontanol and tetracontanol or natural products or extracts from natural products containing them, while the alkanoyl L-carnitine should be selected from the group comprising acetyl, propionyl, butyryl, valeryl and isovaleryl L-carnitine or one of their pharmacologically acceptable salts.

Even more preferably, the polycosanol should be hexacosanol and the alkanoyl L-carnitine propionyl L-carnitine or one of its pharmacologically acceptable salts.

What is meant by pharmacologically acceptable salt of an alkanoyl L-carnitine is any salt of the latter with an acid that does not give rise to unwanted toxic or side effects. These acids are well known to pharmacologists and to experts in pharmacy.

Examples of pharmacologically acceptable salts of alkanoyl L-carnitines, though not exclusively these, are chloride, bromide, orotate, aspartate, acid aspartate, acid citrate, acid phosphate, fumarate and acid fumarate, lactate, maleate and acid maleate, acid oxalate, acid sulphate, glucose phosphate, tartrate and acid tartrate.

One preferred composition, in unit dosage form, is a composition containing 1–100 mg of polycosanols or of natural extracts containing an equivalent amount of the aforesaid polycosanols and 100–2000 mg of L-carnitine or an equivalent amount of alkanoyl L-carnitine.

This new pharmaceutical composition is useful for the prevention and treatment of all those disease conditions related to a high concentration of lipids in tissues such as occurs, for example, in atherosclerosis, hypercholesterolaemia, ischaemic- and atherosclerotic-type cardiovascular disease and peripheral vasculopathies, as well as for the prevention and treatment of diseases related to increased platelet aggregation and to a reduced oxygen concentration, such as, for example, peripheral neuropathy and, in particular, diabetic peripheral neuropathy.

Given here below are the toxicological results of the most significant experimental studies aimed at providing evidence of the surprising and unexpected synergistic effect achieved with the combination of L-carnitine or its derivatives and the above-mentioned polycosanols or natural extracts containing such polycosanols.

TOXICOLOGY 2 g/kg of L-carnitine or 500 mg/kg of hexacosanol, either alone or in combination at the same doses, were administered orally both to rats and to mice, without any mortality among the animals thus treated and without any evident signs of toxicity. Even prolonged daily administrations of carnitine 250 mg/kg or hexacosanol 20 mg/kg, either alone or in combination, for 30 days consecutively failed to produce any signs of toxic reactions or of poor tolerability.

Monitoring of body weight and of blood-chemistry parameters before and during treatment revealed no significant differences as compared to control animals. Moreover, no abnormalities were found at histological examination of the parenchyma of the main organs (heart, lungs, kidneys, adrenal glands and pancreas).

Tests of ATP concentrations in paoillary muscle of rabbits with induced hypoxia

These tests were performed in New Zealand rabbits with a mean body weight of 2 kg, receiving daily intravenous injections of a solution containing 100 mg/kg of L-carnitine or 10 mg/kg of hexacosanol, or of the two substances combined at the same doses, for 3 consecutive days. A group of animals received no treatment and served as the control group.

All the animals treated were sacrificed along with the controls at the end of the third day of treatment two hours after the last injection. The hearts were removed and equal sections of papillary muscle measuring 1 mm in diameter and 4–5 mm in thickness were isolated. These tissues were perfused in a thermostatic bath with a (100%) saturated $O_2$ solution. Experimental hypoxia conditions were induced by introducing $N_2$ (100%) into the bath in place of $O_2$. The ATP content of the papillary muscle was analysed according to the method described by Strehler BL (Methods in Enzymology III—N.Y. Acad. Press, 871, 1957). The analysis was done on tissue samples maintained under normal perfusion conditions for 90 min and after 60 min of hypoxia.

The results obtained in these experiments show that ATP concentrations remain at normal levels only in the group of animals treated with the combination of L-carnitine and hexacosanol, achieving not only a mere additive effect, but a truly synergistic action of L-carnitine plus hexacosanol in protecting the ATP of papillary muscle against the ATP-lowering effect of hypoxia.

TABLE 1

| | ATP content (mol/g tissue) | |
|---|---|---|
| Treatment | Before hypoxia | After hypoxia |
| Controls | 1.65 ± 0.28 | 0.45 ± 0.03 |
| L-carnitine 100 mg/kg | 1.77 ± 0.25 | 0.67 ± 0.02 |
| Hexacosanol 10 mg/kg | 1.70 ± 0.30 | 0.77 ± 0.05 |
| L-carnitine 100 mg/kg + Hexacosanol 10 mg/kg | 1.85 ± 0.27 | 1.58 ± 0.06 |

Tests of cardiac anoxia induced by coronary ligation

These tests were performed to evaluate the protective action of L-carnitine and hexacosanol and their combination on left ventricular arrhythmias due to myocardial anoxia induced by coronary ligation according to the technique described by Selych et cal. (*Angiology* 11–398, 1960) and by Clark et al. (*J Pharmacol Methods* 3–357, 1980). Male Wistar rats with a mean body weight of 350–400 g were submitted to surgical occlusion of the left coronary artery. Arrhythmias set in within 4–7 min of coronary ligation. Ventricular ectopic contractions were then counted during a period of 30 min both in a group of control rats and in the groups of rats receiving slow injection of a solution containing L-carnitine (100 mg/kg), hexacosanol (10 mg/kg) or the two substances in combination at the same doses into the left ventricle 15 min before ligation. It was thus found that the combination of L-carnitine plus hexacosanol injected into the left ventricle was able to produce a dramatic reduction in the number of ectopic contractions (more than 70% reduction compared to controls), whereas administration of L-carnitine or hexacosanol alone showed only a very limited ability to reduce ectopic contractions. These tests also indicate a surprising synergistic effect of the combination of L-carnitine and hexacosanol in affording protection against the damaging effects of anoxia on myocardial contraction.

TABLE 2

| Treatment | Start of arrhythmias (min) | Total ectopic contractions during 30 min after coronary ligation |
|---|---|---|
| Controls | 4–7 | 992 ± 118 |
| L-carnitine 100 mg/kg | 4–7 | 860 ± 202 |
| Hexacosanol 10 mg/kg | 5–7 | 810 ± 190 |
| L-carnitine 100 mg/kg + Hexacosanol 10 mg/kg | 6–7 | 194 ± 112 |

Experimental atherosclerosis tests

These tests, based on induction of experimental atherosclerosis in rats, revealed unexpectedly that the occurrence of the atherosclerosis could be inhibited and thus the induced tissue lesions reduced or inhibited by administering the experimental animals a combination of L-carnitine and hexacosanol. The protection afforded by L-carnitine plus hexacosanol is substantially greater than one might have expected from the sum of the individual effects of the two components. Wistar male rats were used in these tests and the experimental atherosclerosis was induced according to the method suggested by Manilow (*Atherosclerosis* 48: 105, 1983), by administering the rats an atherogenic diet containing 24% casein, 10% cotton oil, 5% salt, 60% sugar, 1% cholesterol, and Vit. $D_2$ 200 m STU/g diet. The anti-atherogenic effect of both L-carnitine and hexacosanol were evaluated by using morphometric methods to measure the thickness of the abdominal aorta and the intensity of the staining induced by Sudan IV, with a 1- to 5-point scoring system, according to the degree of severity. Evidence was thus found to show that both L-carnitine and hexacosanol are capable of reducing the severity of the atherosclerotic lesions, but it is above all the combined use of these two compounds that yields the greatest effect, the combination being capable of reducing or almost entirely inhibiting occurrence of the lesions.

Experimental cholesterolaemia tests

In experimental cholesterolaemia, too, a marked synergistic effect of the L-carnitine plus hexacosanol combination was detected. In these tests, the experimental cholesterolaemia was induced according to the method described by Sirtori (Sirtori CR, *Atherosclerosis* 26–27, 1977). Treatment both With L-carnitine and hexacosanol, as well as with the two compounds in combination, was continued daily for six weeks, in conjunction with a cholesterolaemia-lowering diet. On completing the six weeks of treatment, blood cholesterol was assayed both in control animals put on a cholesterolaemia-lowering diet alone and in animals treated with L-carnitine, or with hexacosanol, or with the two compounds in combination. Using the assay method described by Roschlan (Roschlan P, *Clin Chem Clin Biochem* 12: 403, 1975). The cholesterol values recorded demonstrate that, whereas the cholesterolaemia-inhibiting action of L-carnitine or hexacosanol alone is fairly modest, their combined use exerts a powerful cholesterolaemia-lowering action, thus displaying a marked degree of synergistic action in these tests as well.

TABLE 3

| | Experimental cholesterolaemia tests (total cholesterol mg/dl) |
|---|---|
| Controls | 95.2 ± 5.4 |
| Hypercholesterolaemic controls | 285.7 ± 11.2 |
| L-carnitine 100 mg/kg | 265.5 ± 6.1 |
| Hexacosanol 10 mg/kg | 268.5 ± 5.6 |
| L-carnitine 100 mg/kg + Hexacosanol 10 mg/kg | 146.8 ± 7.1 |

Platelet aggregation inhibition tests

The tests were performed using plasma from healthy volunteers containing at least 300,000 platelets/mm$^3$.

The platelet count was done using a CA 580A Platelet Counter (Delcon). Platelet aggregation was induced using collagen as the aggregating agent at doses of 2.5 and 5 ng/mL according to the technique described by Born and Cross (Born YVR, Cross M, *J Physiol* 26: 25, 1963).

Platelet aggregation was determined photometrically (Born VJR, *Nature* 194: 927, 1962) using an Elvi 840 aggregometer.

Platelet aggregation was measured in basal conditions and after 10 min of incubation with L-carnitine, hexacosanol and the L-carnitine-hexacosanol combination. The aggregant activity induced by collagen (2.5 ng/mL) was not changed by the presence of L-carnitine, whereas hexacosanol proved capable of only partly inhibiting the platelet aggregation induced by collagen ($ED_{50}$ 5.5 ng/ml).

On combining L-carnitine and hexacosanol at the same doses, 100% inhibition of platelet aggregation was achieved. A significant and surprising degree of synergy between L-carnitine and hexacosanol was thus observed in the inhibition of platelet aggregation.

The weight-to-weight ratio between L-carnitine or an alkanoyl L-carnitine or one of their pharmacologically acceptable salts and hexacosanol may vary within a broad range. Preferably, this ratio should range from 1:1 to 2000:1. One preferred ratio is 50:1.

Non-limiting examples of compositions according to the present invention are given here below. For the purposes of brevity and simplicity of description, reference will be made only to L-carnitine, it being understood that the compositions described also apply to the above-mentioned alkanoyl L-carnitines and to the pharmacologically acceptable salts of both L-carnitine and the above-mentioned alkanoyl L-carnitines.

| 1) | L-carnitine | 250 mg |
|---|---|---|
| | Hexacosanol | 5 mg |
| 2) | L-carnitine | 500 mg |
| | Hexacosanol | 10 mg |
| 3) | L-carnitine | 125 mg |
| | Natural extract of sugar cane standardised in hexacosanol equal to | 10 mg |
| 4) | L-carnitine | 250 mg |
| | Wheat germ extract standardised in hexacosonal equal to | 10 mg |
| 5) | L-carnitine | 250 mg |
| | Rice germ extract standardised in hexacosanol equal to | 10 mg |
| 6) | L-carnitine | 250 mg |
| | Hexacosanol | 5 mg |
| | Vit. E | 5 mg |
| | Vit. $B_1$ | 1 mg |
| | Vit. $B_2$ | 1 mg |
| | Vit. A | 1 mg |
| | Calcium pantothenate | 10 mg |
| | Magnesium | 10 mg |
| | Selenium | 2 mg |
| | Zinc | 1 mg |
| | Manganese | 1 mg |

What is claimed is:

1. A method of preventing or treating a disease caused by abnormal lipid metabolism, by increased platelet aggregation and by ischemic tissue damage due to decreased oxygen concentration, said process comprising the coordinated administration to a patient in need thereof an effective amount of L-carnitine or a pharmacologically acceptable salt thereof and hexacosanol.

2. A method of preventing or treating a disease caused by abnormal lipid metabolism, by increased platelet aggregation and by ischemic tissue damage due to decreased oxygen concentration, said process comprising the coordinated administration to a patient in need thereof an effective amount of L-carnitine or a pharmacologically acceptable salt thereof and a hexacosanol obtained from a plant selected from the group consisting of sugar cane, wheat germ and rice germ.

3. The method of claim 1 or 2, wherein the pharmacologically acceptable salt of L-carnitine is selected from the group consisting of chloride, bromide, orotate, aspartate, acid aspartate, acid citrate, acid phosphate, fumarate and acid fumarate, lactate, maleate and acid maleate, acid oxalate, acid sulphate, glucose phosphate, tartrate and acid tartrate.

4. An orally administerable composition for preventing or treating a disease caused by abnormal lipid metabolism, by increased platelet aggregation and by ischemic tissue damage due to decreased oxygen concentration, said composition consisting essentially of an effective amount of L-carnitine or a pharmacologically acceptable salt thereof and a hexacosanol obtained from a plant selected from the group consisting of sugar cane, wheat germ and rice germ.

5. An orally administerable composition for treating a disease caused by abnormal lipid metabolism, by increased platelet aggregation and by ischemic tissue damage due to decreased oxygen concentration, said composition consisting essentially of an effective amount of L-carnitine or a pharmacologically acceptable salt thereof and hexacosanol.

6. The composition of claim 4 or 5, wherein the pharmacologically acceptable salt of L-carnitine is selected from the group consisting of chloride, bromide, orotate, aspartate, acid aspartate, acid citrate, acid phosphate, fumarate and acid fumarate, lactate, maleate and acid maleate, acid oxalate, acid sulphate, glucose phosphate, tartrate and acid tartrate.

* * * * *